US012220159B2

(12) United States Patent
Sawyer et al.

(10) Patent No.: US 12,220,159 B2
(45) Date of Patent: Feb. 11, 2025

(54) SURGICAL INSTRUMENT WITH ECCENTRIC CAM

(71) Applicant: COVIDIEN LP, Mansfield, MA (US)

(72) Inventors: Alyssa M. Sawyer, Broomfield, CO (US); Purvishkumar H. Soni, Longmont, CO (US)

(73) Assignee: Covidien LP, Mansfield, MA (US)

( * ) Notice: Subject to any disclaimer, the term of this patent is extended or adjusted under 35 U.S.C. 154(b) by 1205 days.

(21) Appl. No.: 16/354,594

(22) Filed: Mar. 15, 2019

(65) Prior Publication Data
US 2020/0289192 A1  Sep. 17, 2020

(51) Int. Cl.
| | |
|---|---|
| *A61B 17/28* | (2006.01) |
| *A61B 17/29* | (2006.01) |
| *A61B 18/08* | (2006.01) |
| *A61B 18/12* | (2006.01) |
| *A61B 18/14* | (2006.01) |
| *A61B 18/00* | (2006.01) |

(52) U.S. Cl.
CPC ........ *A61B 18/1445* (2013.01); *A61B 17/282* (2013.01); *A61B 17/2909* (2013.01);
(Continued)

(58) Field of Classification Search
CPC .............. A61B 18/1445; A61B 18/085; A61B 18/1206; A61B 17/282;
(Continued)

(56) References Cited

U.S. PATENT DOCUMENTS

| | | |
|---|---|---|
| D249,549 S | 9/1978 | Pike |
| D263,020 S | 2/1982 | Rau, III |
| | (Continued) | |

FOREIGN PATENT DOCUMENTS

| | | |
|---|---|---|
| CN | 201299462 Y | 9/2009 |
| DE | 2415263 A1 | 10/1975 |
| | (Continued) | |

OTHER PUBLICATIONS

Michael Choti, "Abdominoperineal Resection with the LigaSure Vessel Sealing System and LigaSure Atlas 20 cm Open Instrument"; Innovations That Work, Jun. 2003.
(Continued)

*Primary Examiner* — Joseph A Stoklosa
*Assistant Examiner* — Annie L Shoulders (57) ABSTRACT

A forceps includes a housing, an elongated shaft assembly, and a cam assembly. The housing includes a movable handle pivotally coupled to the housing. The elongated shaft assembly is coupled to the housing and extends distally to support jaw members at a distal end thereof. One or both of the jaw members is selectively moveable relative to the other jaw member between a spaced apart position for manipulating tissue and a closed position for compressing tissue therebetween. The cam assembly is supported in the housing and includes an eccentric cam cable and an eccentric cam. The eccentric cam cable is operably coupled to the movable handle and positioned to rotate the eccentric cam upon movement thereof, wherein rotation of the eccentric cam reduces an amount of force on the movable handle required to move the jaw members to the closed position to compress tissue disposed between the jaw members.

20 Claims, 5 Drawing Sheets

(52) U.S. Cl.
CPC ........ *A61B 18/085* (2013.01); *A61B 18/1206* (2013.01); *A61B 18/1482* (2013.01); *A61B 2017/2913* (2013.01); *A61B 2017/2946* (2013.01); *A61B 2018/00083* (2013.01); *A61B 2018/00589* (2013.01); *A61B 2018/00595* (2013.01); *A61B 2018/00601* (2013.01); *A61B 2018/00619* (2013.01); *A61B 2018/0063* (2013.01); *A61B 2018/00916* (2013.01); *A61B 2018/1412* (2013.01); *A61B 2018/1455* (2013.01)

(58) Field of Classification Search
CPC ........... A61B 2018/00083; A61B 2018/00601; A61B 2018/00916; A61B 2018/1412; A61B 2018/1455; A61B 2017/2913; A61B 2017/2946
See application file for complete search history.

(56) References Cited

U.S. PATENT DOCUMENTS

| | | | |
|---|---|---|---|
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| 5,452,836 A * | 9/1995 | Huitema | A61B 17/072 227/176.1 |
| 5,465,894 A * | 11/1995 | Clark | A61B 17/072 227/19 |
| D384,413 S | 9/1997 | Zlock et al. | |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| 6,533,772 B1 * | 3/2003 | Sherts | A61M 25/0136 279/42 |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| 7,255,697 B2 | 8/2007 | Dycus et al. | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| D661,394 S | 6/2012 | Romero et al. | |
| D670,808 S | 11/2012 | Moua et al. | |
| D680,220 S | 4/2013 | Rachlin | |
| 8,828,023 B2 | 9/2014 | Neff et al. | |
| 9,084,608 B2 | 7/2015 | Larson et al. | |
| 9,211,657 B2 | 12/2015 | Ackley et al. | |
| 9,655,673 B2 | 5/2017 | McCullough, Jr. et al. | |
| 9,820,765 B2 | 11/2017 | Allen, IV et al. | |
| 2010/0010512 A1 * | 1/2010 | Taylor | A61B 17/0491 606/144 |
| 2014/0221995 A1 | 8/2014 | Guerra et al. | |
| 2014/0221999 A1 | 8/2014 | Cunningham et al. | |
| 2014/0228842 A1 | 8/2014 | Dycus et al. | |
| 2014/0230243 A1 | 8/2014 | Roy et al. | |
| 2014/0236149 A1 | 8/2014 | Kharin et al. | |
| 2014/0243811 A1 | 8/2014 | Reschke et al. | |
| 2014/0243824 A1 | 8/2014 | Gilbert | |
| 2014/0249528 A1 | 9/2014 | Hixson et al. | |
| 2014/0250686 A1 | 9/2014 | Hempstead et al. | |
| 2014/0257274 A1 | 9/2014 | McCullough, Jr. et al. | |
| 2014/0257283 A1 | 9/2014 | Johnson et al. | |
| 2014/0257284 A1 | 9/2014 | Artale | |
| 2014/0257285 A1 | 9/2014 | Moua | |
| 2014/0257326 A1 * | 9/2014 | Kokish | A61M 25/0662 74/30 |
| 2014/0276803 A1 | 9/2014 | Hart | |
| 2014/0284313 A1 | 9/2014 | Allen, IV et al. | |
| 2014/0288549 A1 | 9/2014 | McKenna et al. | |
| 2014/0288553 A1 | 9/2014 | Johnson et al. | |
| 2014/0330308 A1 | 11/2014 | Hart et al. | |
| 2014/0336635 A1 | 11/2014 | Hart et al. | |
| 2014/0353188 A1 | 12/2014 | Reschke et al. | |
| 2015/0018816 A1 | 1/2015 | Latimer | |
| 2015/0025528 A1 | 1/2015 | Arts | |
| 2015/0032106 A1 | 1/2015 | Rachlin | |
| 2015/0051598 A1 | 2/2015 | Orszulak et al. | |
| 2015/0051640 A1 | 2/2015 | Twomey et al. | |
| 2015/0066026 A1 | 3/2015 | Hart et al. | |
| 2015/0080880 A1 | 3/2015 | Sartor et al. | |
| 2015/0080889 A1 | 3/2015 | Cunningham et al. | |
| 2015/0082928 A1 | 3/2015 | Kappus et al. | |
| 2015/0088122 A1 | 3/2015 | Jensen | |
| 2015/0088126 A1 | 3/2015 | Duffin et al. | |
| 2015/0088128 A1 | 3/2015 | Couture | |
| 2015/0094714 A1 | 4/2015 | Lee et al. | |
| 2015/0313667 A1 * | 11/2015 | Allen, IV | A61B 18/1445 606/41 |
| 2016/0089127 A1 * | 3/2016 | Kirkemo | A61B 1/0052 606/110 |
| 2017/0224343 A1 * | 8/2017 | Baxter, III | A61B 17/105 |
| 2017/0231653 A1 * | 8/2017 | Kapadia | A61B 34/71 606/208 |
| 2017/0303921 A1 * | 10/2017 | Patel | A61B 17/1285 |
| 2018/0214200 A1 * | 8/2018 | Nanditale Gurumurthy | A61B 17/282 |
| 2020/0138532 A1 * | 5/2020 | Podolsky | A61B 34/71 |

FOREIGN PATENT DOCUMENTS

| | | | |
|---|---|---|---|
| DE | 02514501 A1 | 10/1976 | |
| DE | 2627679 A1 | 1/1977 | |
| DE | 03423356 C2 | 6/1986 | |
| DE | 03612646 A1 | 4/1987 | |
| DE | 3627221 A1 | 2/1988 | |
| DE | 8712328 U1 | 3/1988 | |
| DE | 04303882 C2 | 2/1995 | |

(56) References Cited

FOREIGN PATENT DOCUMENTS

| | | |
|---|---|---|
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A2 | 3/2003 |
| JP | 401367 A1 | 11/1974 |
| JP | 61501068 | 9/1984 |
| JP | 1024051 A | 1/1989 |
| JP | 1147150 A | 6/1989 |
| JP | 6502328 | 3/1992 |
| JP | 55106 | 1/1993 |
| JP | H0540112 A | 2/1993 |
| JP | 6121797 A | 5/1994 |
| JP | 6285078 A | 10/1994 |
| JP | 6511401 | 12/1994 |
| JP | H06343644 A | 12/1994 |
| JP | H07265328 A | 10/1995 |
| JP | 08056955 | 3/1996 |
| JP | 08252263 A | 10/1996 |
| JP | 8289895 A | 11/1996 |
| JP | 8317934 A | 12/1996 |
| JP | 8317936 A | 12/1996 |
| JP | 09000538 A | 1/1997 |
| JP | H0910223 A | 1/1997 |
| JP | 9122138 A | 5/1997 |
| JP | 0010000195 A | 1/1998 |
| JP | 10155798 A | 6/1998 |
| JP | 1147149 | 2/1999 |
| JP | 11070124 A | 3/1999 |
| JP | 11169381 A | 6/1999 |
| JP | 11192238 A | 7/1999 |
| JP | H11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001008944 | 1/2001 |
| JP | 2001029355 | 2/2001 |
| JP | 2001029356 | 2/2001 |
| JP | 2001003400 | 4/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011125195 A | 6/2011 |
| JP | H0630945 B2 | 11/2016 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 | 6/2002 |
| WO | 2006021269 A1 | 3/2006 |
| WO | 2005110264 A2 | 4/2006 |
| WO | 2008040483 A1 | 4/2008 |
| WO | 2011018154 A1 | 2/2011 |
| WO | 2016025132 A1 | 2/2016 |

OTHER PUBLICATIONS

Chung et al., "Clinical Experience of Sutureless Closed Hemorrhoidectomy with LigaSure" Diseases of the Colon & Rectum vol. 46, No. Jan. 1, 2003.

Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000. (6 pages).

Johnson et al. "Evaluation of a Bipolar Electrothermal Vessel Sealing Device in Hemorrhoidectomy" Sales/Product Literature; Jan. 2004. (1 page).

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Burdette et al. "In Vivo Probe Measurement Technique For Determining Dielectric Properties At VHF Through Microwave Frequencies", IEEE Transactions on Microwave Theory and Techniques, vol. MTT-28, No. 4, Apr. 1980 pp. 414-427.

Carus et al., "Initial Experience With the LigaSure Vessel Sealing System in Abdominal Surgery" Innovations That Work, Jun. 2002.

Heniford et al. "Initial Results with an Electrothermal Bipolar Vessel Sealer" Surgical Endoscopy (2000) 15:799-801. (4 pages).

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

(56) References Cited

OTHER PUBLICATIONS

Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. Jul. 1, 2001; pp. 21-24.
Levy et al., "Update on Hysterectomy—New Technologies and Techniques" OBG Management, Feb. 2003. (15 pages).
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surger" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
U.S. Appl. No. 08/926,869; filed Sep. 10, 1997; inventor: James G. Chandler, Abandoned.
U.S. Appl. No. 09/177,950; filed Oct. 23, 1998; inventor: Randel A. Frazier, abandoned.
U.S. Appl. No. 09/387,883; filed Sep. 1, 1999; inventor: Dale F. Schmaltz, abandoned.
U.S. Appl. No. 09/591,328; filed Jun. 9, 2000; inventor: Thomas P. Ryan, abandoned.
U.S. Appl. No. 12/336,970; filed Dec. 17, 2008; inventor: Paul R. Sremcich, abandoned.
U.S. Appl. No. 14/065,644; filed Oct. 29, 2013; inventor: Reschke, abandoned.
Heniford et al. "Initial Research and Clinical Results with an Electrothermal Bipolar Vessel Sealer" Oct. 1999.

\* cited by examiner

SURGICAL INSTRUMENT WITH ECCENTRIC CAM

TECHNICAL FIELD

This disclosure relates generally to the field of surgical instruments, and in particular, to surgical instruments such as endoscopic electrosurgical forceps that are economical to manufacture and use, for instance, to seal and cut tissue structures.

BACKGROUND

Instruments such as electrosurgical forceps are commonly used in open and endoscopic surgical procedures to coagulate, cauterize and seal tissue. Such forceps typically include a pair of jaw members that can be controlled by a surgeon to grasp targeted tissue, such as, e.g., a blood vessel. The jaw members may be approximated to apply a mechanical clamping force to the tissue, and are associated with at least one electrode to enable the delivery of electrosurgical energy to the tissue. The combination of the mechanical clamping force and the electrosurgical energy has been demonstrated to join adjacent layers of tissue captured between the jaw members. When the adjacent layers of tissue include the walls of a blood vessel, sealing the tissue may result in hemostasis, which may facilitate the transection of the sealed tissue. A detailed discussion of the use of an electrosurgical forceps may be found in U.S. Pat. No. 7,255,697 to Dycus et al.

A bipolar electrosurgical forceps typically includes opposed electrodes disposed on clamping faces or tissue engaging surfaces of the jaw members. The electrodes are charged to opposite electrical potentials such that an electrosurgical current may be selectively transferred through tissue grasped between the electrodes. To effectuate a proper seal, particularly in relatively large vessels, two mechanical parameters that should be controlled are the pressure applied to the vessel and the gap distance established between the electrodes.

Both the pressure and the gap distance influence the effectiveness of the resultant tissue seal. If an adequate gap distance is not maintained, there is a possibility that the opposed electrodes will contact one another, which may cause a short circuit and prevent energy from being transferred through the tissue. Also, if too low a force is applied, the tissue may have a tendency to move before an adequate seal can be generated. The gap distance between tissue engaging surfaces of a typical effective tissue seal is optimally between about 0.001 and about 0.010 inches. Below this range, the seal may shred or tear, and above this range, the vessel walls may not be effectively joined. Closure pressures for sealing large tissue structures typically fall within the range of about 3 kg/cm$^2$ to about 16 kg/cm$^2$.

SUMMARY

According to one aspect, this disclosure is directed to a forceps including a housing, an elongated shaft assembly, and a cam assembly. The housing includes a movable handle pivotally coupled to the housing. The elongated shaft assembly is coupled to the housing and extends distally to support a pair of jaw members at a distal end thereof. One or both of the jaw members is selectively moveable relative to the other jaw member between a spaced apart position for manipulating tissue and a closed position for compressing tissue therebetween. The cam assembly is supported in the housing and includes an eccentric cam cable and an eccentric cam. The eccentric cam cable is operably coupled to the movable handle and positioned to rotate the eccentric cam upon movement thereof, wherein rotation of the eccentric cam reduces an amount of force on the movable handle required to move the jaw members to the closed position to compress tissue disposed between the jaw members.

In embodiments, the cam assembly may further include an annular cam positioned adjacent to the eccentric cam. The eccentric cam and the annular cam may be disposed on a shaft that is pivotally supported within the housing. The eccentric cam may include an inner eccentric cam plate and an outer eccentric cam plate that are configured to maintain the eccentric cam cable on an eccentric track defined between the inner and outer eccentric cam plates. The eccentric track may include an annular portion and a triangular portion. The annular portion and the triangular portion of the eccentric track may define a tear-dropped shaped profile.

In some embodiments, the annular cam may include an annular track defined therein including substantially the same diameter as the annular portion of the eccentric track.

In various embodiments, the forceps may further include an annular cam cable that is supported on the annular track of the annular cam. The elongated shaft assembly may extend into the housing and may support an inner shaft that operatively couples to the pair of jaw members. The inner shaft may support a collar that couples to the annular cam cable.

In embodiments, the forceps may further include a compression spring supported on the inner shaft. The compression spring may be engaged with the collar and an arm of the movable handle to spring bias the movable handle.

According to yet another aspect of this disclosure, an electrosurgical system includes a housing, an elongated shaft assembly, an annular cam, an eccentric cam. The housing includes a movable handle. The movable handle is coupled to the housing and pivotable between a distal position and a proximal position relative to the housing. The elongated shaft assembly is coupled to the housing and extends distally to an end effector. The end effector has a pair of jaw members movable between an open position and a closed position in response to movement of the movable handle between the distal and proximal positions. The annular cam is supported in the housing and coupled to the elongated shaft assembly. The eccentric cam is coupled to the annular cam and positioned to rotate with the eccentric cam as the movable handle pivots between the distal and proximal positions.

In embodiments, the elongated shaft assembly may include an inner shaft, wherein rotation of the annular cam may cause the inner shaft to axially translate between distal and proximal positions relative to the housing to actuate the pair of jaw members.

In some embodiments, the forceps may further include an annular cam cable coupled to the annular cam and a collar supported on the inner shaft. The inner shaft may support a compression spring engaged with the collar and the movable handle.

In various embodiments, the forceps may further include an eccentric cam cable coupled to the eccentric cam and to the movable handle.

In some embodiments, the annular cam and the eccentric cam may have different profiles. Rotation of the eccentric cam may change a jaw force ratio as the movable handle pivots relative to the eccentric cam.

In embodiments, the pair of jaw members may be configured to receive electrosurgical energy to selectively seal tissue disposed between the pair of jaw members.

In various embodiments, the forceps may further include a knife assembly that is actuatable to sever tissue disposed between the pair of jaw members.

According to yet another aspect of this disclosure, a forceps system includes a generator and a forceps. The forceps is coupled to the generator and includes a housing, a movable handle coupled to the housing, and an elongated shaft assembly that extends distally from the housing to a pair of jaw members at a distal end thereof. The pair of jaw members is disposed in electrical communication with the generator. The pair of jaw members is movable between a spaced apart position for manipulating tissue and a closed position for compressing tissue therebetween. The forceps further includes an eccentric cam coupled to the movable handle and positioned to rotate as the movable handle pivots between distal and proximal positions relative to the housing. Rotation of the eccentric cam relative to the movable handle reduces an amount of force on the movable handle required to move the pair of jaw members to a closed position to compress tissue disposed between the pair of jaw members.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with the detailed description of the embodiments given below, serve to explain the principles of the disclosure.

DETAILED DESCRIPTION

Embodiments of the disclosed electrosurgical forceps are described in detail with reference to the drawings, in which like reference numerals designate identical or corresponding elements in each of the several views. As commonly known, the term "clinician" refers to a doctor, a nurse, or any other care provider and may include support personnel. Further, as is used in the art, the term "distal" refers to a position, a direction, and/or a structure, which is farther from the user, and the term "proximal" refers to a position, a direction, and/or a structure, which is closer to the user. In addition, directional terms such as upper, lower, front, rear, top, bottom, up, down, right, left, and the like are used simply for convenience of description and are not intended to limit this disclosure.

Figure 1A:
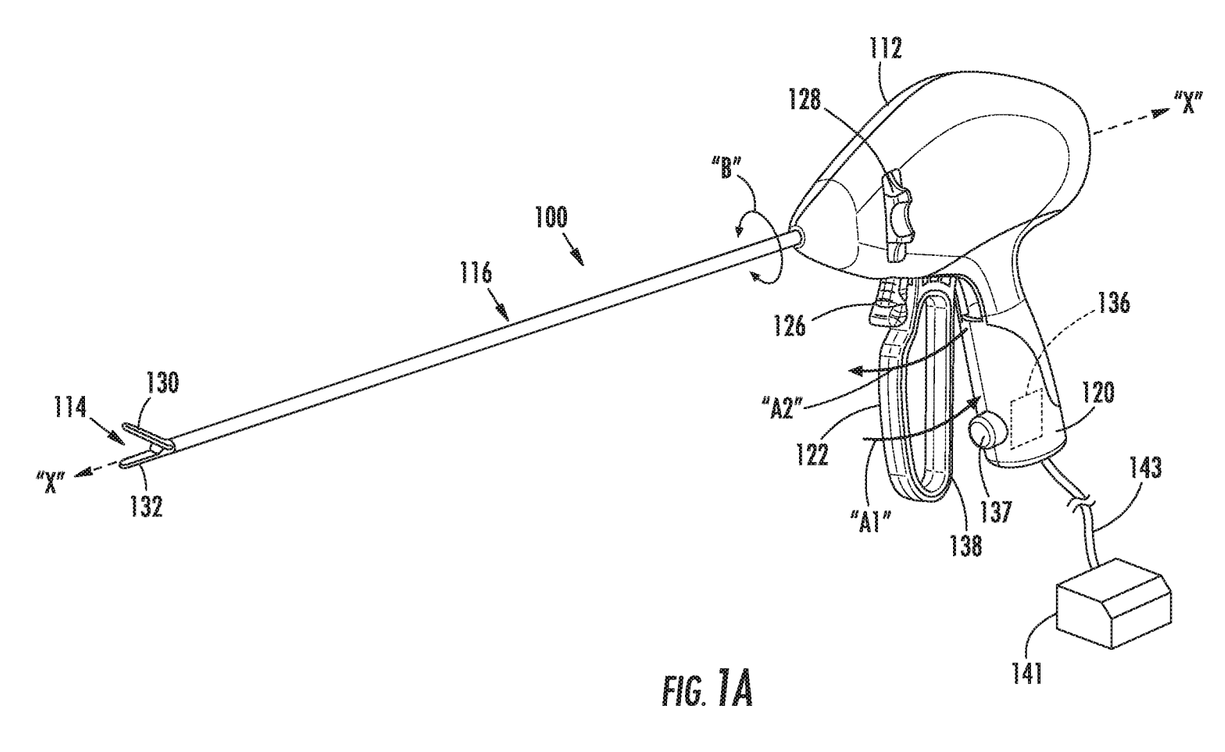
FIG. 1A is a perspective view of an electrosurgical forceps according to the principles of the disclosure.
Figure 1B:
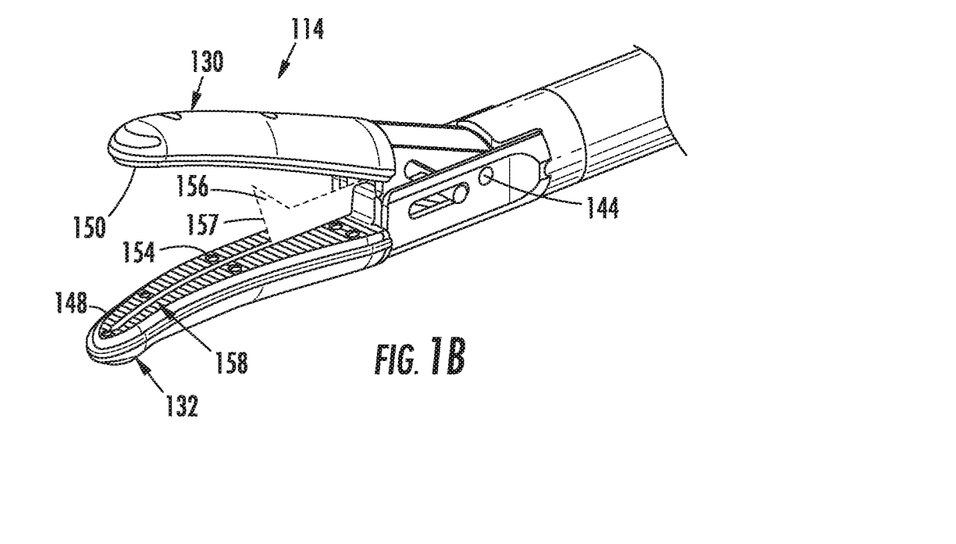
FIG. 1B is an enlarged, perspective view of an end effector of the electrosurgical forceps of FIG. 1A, the end effector illustrated in an open position.
Figure 1C:
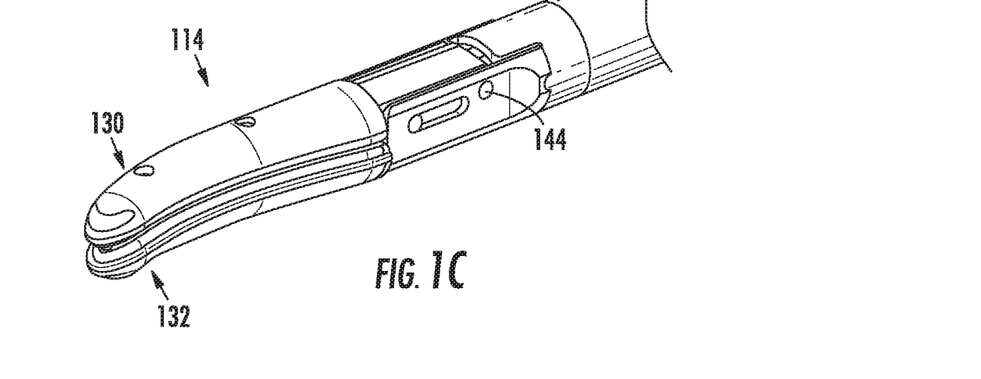
FIG. 1C is an enlarged, perspective view of the end effector of FIG. 1B illustrated in a closed position.

Referring initially to FIGS. 1A-1C, an electrosurgical forceps 100 defines a longitudinal axis "X-X" and generally includes an instrument housing 112, an elongated shaft assembly 116 that extends from instrument housing 112, and an end effector 114 supported on a distal end of elongated shaft assembly 116. Instrument housing 112 supports various actuators for remotely controlling end effector 114 through elongated shaft assembly 116. Although this configuration is typically associated with instruments for use in laparoscopic or endoscopic surgical procedures, various aspects of this disclosure may be practiced in connection with endoluminal procedures and with traditional open instruments.

To mechanically control end effector 114 of electrosurgical forceps 100, instrument housing 112 supports a stationary handle 120, a movable handle 122, a trigger 126 and a rotation knob assembly 128. Movable handle 122 of instrument housing 112 is operable to move end effector 114 between an open position (FIGS. 1A and 1B) in which a pair of opposed jaw members 130, 132 are disposed in spaced relation relative to one another, and a closed or clamping position (FIG. 1C) in which jaw members 130, 132 are closer together. Approximation of movable handle 122 toward stationary handle 120, as indicated by arrow "A1," serves to move end effector 114 to the closed position. Separation of movable handle 122 away from stationary handle 120, as indicated by arrow "A2," serves to move end effector 114 to the open position. Trigger 126 is operable to extend and retract a knife blade 156 (FIG. 1B) through end effector 114 when end effector 114 is in the closed position (FIG. 1C). Rotation knob assembly 128 serves to rotate elongated shaft assembly 116 and end effector 114 about longitudinal axis "X-X" of electrosurgical forceps 100 as rotation knob assembly 128 rotates about longitudinal axis "X-X," as indicated by arrows "B."

To electrically control end effector 114 of electrosurgical forceps 100, stationary handle 120 of instrument housing 112 of forceps 100 supports a depressible button 137 that is operable by a clinician to selectively initiate and terminate delivery of electrosurgical energy to end effector 114. Depressible button 137 is mechanically coupled to a switch 136 disposed within stationary handle 120. Upon proximal movement of moveable handle 122 toward an actuated or proximal position, as illustrated by arrow "A1," button 137 is configured to engage a button activation post 138 that extends from a proximal side of moveable handle 122. Switch 136 is in electrical communication with an electrosurgical generator 141 via a cable 143 that extends from instrument housing 112.

End effector 114 of electrosurgical forceps 100 may be moved from an open position (FIG. 1B), in which tissue (not shown) can be received between jaw members 130, 132 of end effector 114, and a closed position (FIG. 1C), in which tissue can be clamped and treated with electrosurgical energy delivered from generator 141. Jaw members 130, 132 pivot about a pivot pin 144 to move end effector 114 to the closed position (FIG. 2B) in which sealing plates 150, 148 of respective jaw members 130, 132 provide a pressure to tissue grasped between jaw members 130, 132. In some embodiments, to provide an effective tissue seal, a pressure within a range between about 3 kg/cm$^2$ to about 16 kg/cm$^2$ and, typically, within a working range of about 7 kg/cm$^2$ to about 13 kg/cm$^2$, may be applied by end effector 114 to the tissue. Also, in the closed position, a separation or gap distance is maintained between the sealing plates 148, 150 by an array of stop members 154 (FIG. 1B) disposed on or adjacent to sealing plates 148, 150. Stop members 154 contact opposing surfaces of jaw members 130, 132 and prevent further approximation of sealing plates 148, 150. In some embodiments, to provide an effective tissue seal, an appropriate gap distance of about 0.001 inches to about 0.010 inches and, typically, between about 0.003 inches to about 0.006 inches, may be provided. In some embodiments, stop members 154 are constructed of a heat-resistant ceramic deposited onto jaw members 130, 132. In other embodiments, stop members 154 are constructed of an electrically non-conductive plastic molded onto jaw members 130, 132 by a process such as overmolding or injection molding. Stop members 154 may be provided in any suitable number, arrangement, and/or configuration.

Upper and lower jaw members 130, 132 of end effector 114 are electrically coupled to generator 141 to provide an electrical pathway to opposed tissue-engaging sealing plates 148, 150 of lower and upper jaw members 132, 130, respectively. In some embodiments, sealing plates 148 and 150 are electrically coupled to opposite terminals, for example, positive or active (+) and negative or return (−) terminals associated with generator 141 so that bipolar energy may be provided through sealing plates 148, 150 to tissue. Alternatively, sealing plates 148, 150 may be configured to deliver monopolar energy to tissue. In a monopolar configuration, one or both sealing plates 148, 150 deliver electrosurgical energy from an active terminal (+) while a return pad (not shown) is placed generally on a patient and provides a return path to the opposite terminal (−) of generator 141.

Electrosurgical energy may be delivered to tissue through electrically conductive seal plates 148, 150 to effectuate a tissue seal. Once a tissue seal is established, a knife blade 156 having a sharpened distal edge 157 may be advanced through a knife channel 158 defined in one or both jaw members 130, 132 to transect sealed tissue. Although knife blade 156 is depicted in FIG. 1B as extending from elongated shaft assembly 116 when end effector 114 is in an open position, in some embodiments, extension of knife blade 156 into knife channel 158 when end effector 114 is in the open position is prevented.

For a more detailed description of a similar electrosurgical forceps, or components thereof, reference can be made, for example, to U.S. Pat. No. 9,655,673 to McCullough, Jr. et al. and U.S. Pat. No. 9,820,765 to Allen et al., the entire contents of each of which are incorporated herein by reference.

Figure 2:
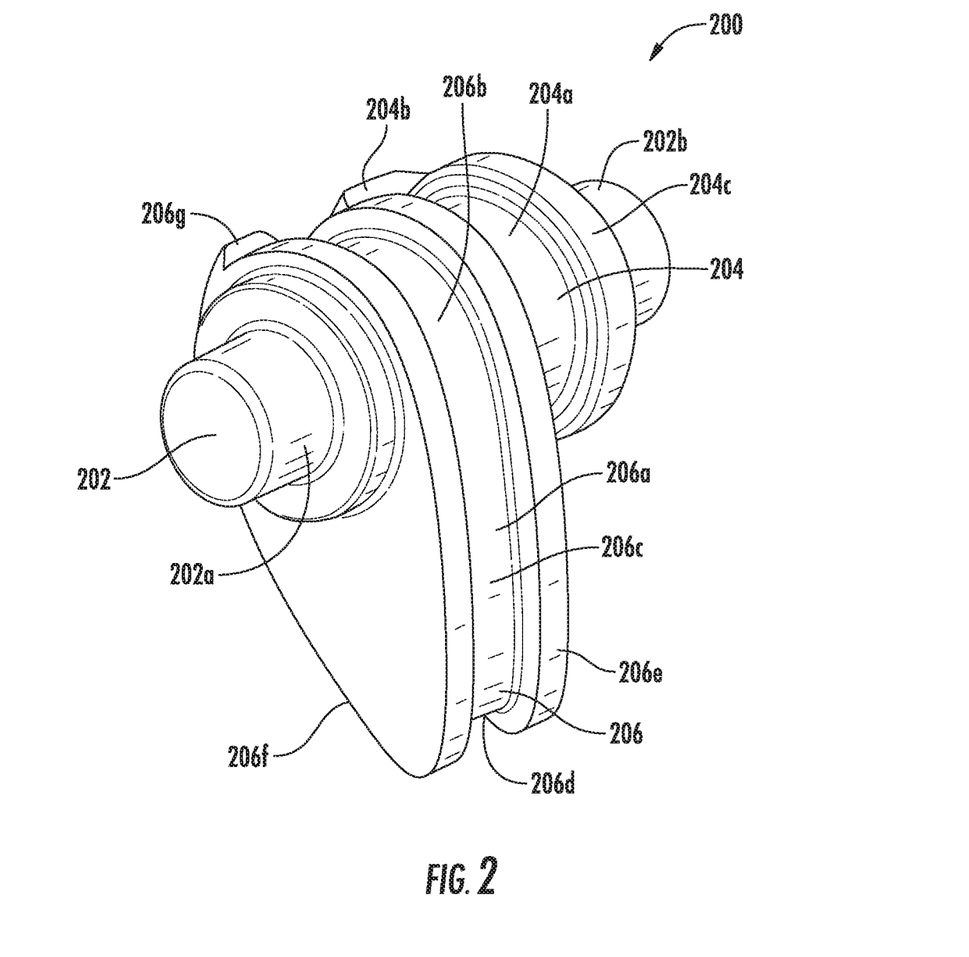
FIG. 2 is an enlarged, perspective view of a cam assembly of the electrosurgical forceps of FIG. 1A.
Figure 3A:
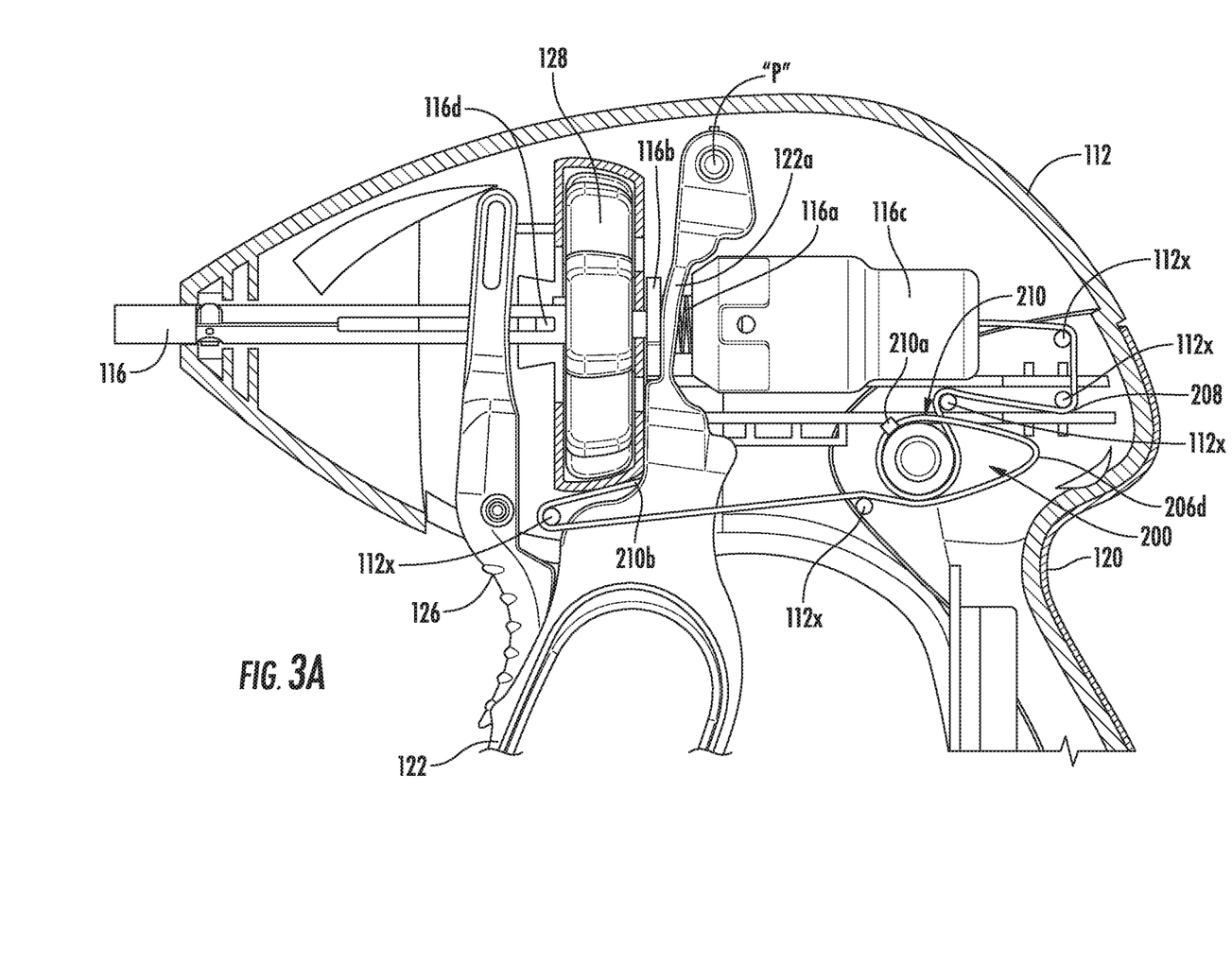
FIGS. 3A and 3B are progressive views illustrating the cam assembly of FIG. 2 moving between unactuated and actuated positions relative to an instrument housing of the electrosurgical forceps of FIG. 1A.
Figure 3B:
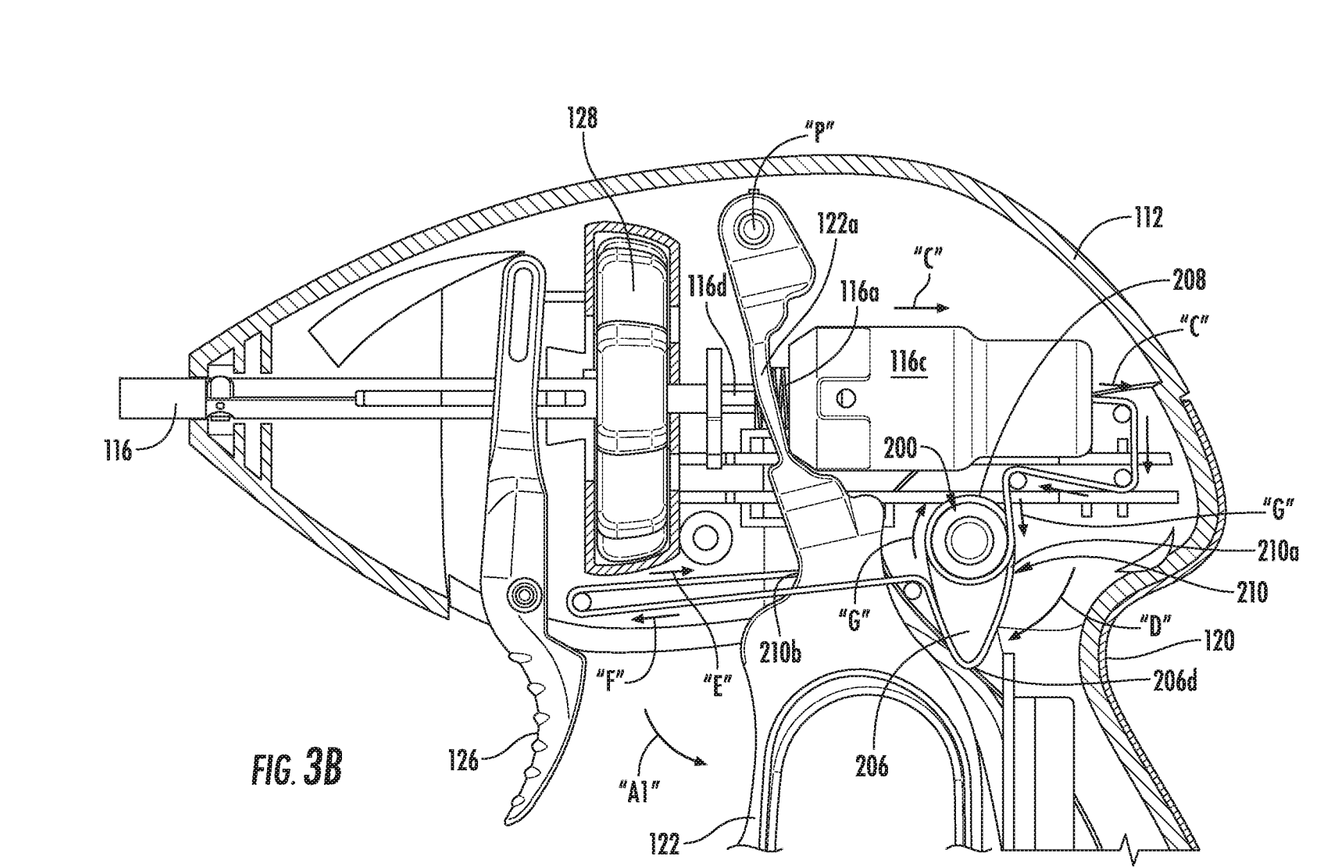

Referring now to FIGS. 2, 3A, and 3B, instrument housing 112 further supports a cam assembly 200 that is pivotally coupled to instrument housing 112. Cam assembly 200, which may be formed (e.g., integrally) using any suitable manufacturing technique such as injection molding, welding, casting, machining, joining, additive printing, etc., or combinations thereof, includes a shaft 202 that supports an annular cam 204 and an eccentric cam 206. In some embodiments, shaft 202, annular cam 204 and eccentric cam 206, may be monolithically formed.

Shaft 202 of cam assembly 200 includes opposite ends 202a, 202b that extend from opposite sides of cam assembly 200 to pivotally couple cam assembly 200 to instrument housing 112 by any suitable mechanical coupling such as pin holes (not shown) defined in instrument housing 112 that receive opposite ends 202a, 202b of shaft 202.

Annular cam 204 of cam assembly 200 includes an annular track 204a, which may be supported concentrically about shaft 202 of cam assembly 200. Annular track 204a has an annular profile (e.g., circular) with a diameter that can be greater than a diameter of shaft 202. Annular cam 204 further includes a cable attachment portion 204b that secures a first end portion of annular cam cable 208 to annular cam 204. Annular cam cable 208 is wound about annular track 204a. Annular cam cable 208 extends from annular track 204a and is redirected about any number of inner bars 112x (e.g., three) extending from instrument housing 112 of forceps 100 at various locations along an inner surface of instrument housing 112 so that a second end portion of annular cam cable 208 couples to a collar 116c supported on proximal end portion of elongated shaft assembly 116 of forceps 100. Annular cam 204 also includes an outer cam plate 204c positioned adjacent to annular track 204a. Outer cam plate 204c has a diameter greater than a diameter of annular track 204a to prevent annular cam cable 208 from sliding off annular track 204a.

Eccentric cam 206 of cam assembly 200 includes an eccentric track 206a having an eccentric profile (e.g., tear drop-shaped, pear-shaped, kite-shaped, egg-shaped, etc.). The eccentric profile of eccentric track 206a is defined by an annular portion 206b supported (e.g., concentrically) about shaft 202 of cam assembly 200 and a triangular portion 206c. Triangular portion 206c extends from annular portion 206b to an apex 206d. Triangular and annular portions 206b, 206c of eccentric track 206a may be coplanar. Eccentric track 206a is supported between an inner eccentric cam plate 206e and an outer eccentric cam plate 206f. An eccentric cam cable 210 is configured to cam along eccentric track 206a. Eccentric cam cable 210 is wound about eccentric track 206a of eccentric cam 206. Eccentric cable 210 extends from eccentric track 206a and is redirected by any number of inner bars 112x of instrument housing 112 (e.g., two). More particularly, a first end portion 210a of cable 210 is secured to a cable attachment portion 206g of eccentric cam 206 so that cable 210 can be wound about eccentric cam 206. A second end portion 210b of cable 210 extends from eccentric cam 206 and is secured to movable handle 122. Eccentric track 206a is recessed from inner and outer eccentric cam plates 206e, 206f so that inner and outer eccentric cam plates 206e, 206f prevent eccentric cam cable 210 from sliding off of eccentric track 206a as eccentric cam cable 210 cams along eccentric track 206a of eccentric cam 206.

With reference to FIGS. 3A and 3B, a proximal end portion of elongated shaft assembly 116 supports a compression spring 116a, a stop tab 116b and a collar 116c within instrument housing 112. Compression spring 116a is supported between an arm 122a of movable handle 122 and collar 116c to urge movable handle 122 in a distal direction to bias end effector 114 (FIG. 1) toward its open position. Arm 122a of movable handle 122 is selectively engagable with stop tab 116b to limit distal movement of moveable handle 122 as seen in FIG. 3A.

In order to approximate jaw members 130, 132 of end effector 114, movable handle 122 is pivoted about pivot point "P," as indicated by arrows "A1," between a distal position (FIG. 3A) in which end effector 114 is in an open position (FIG. 1B), and a proximal position (FIG. 3B) in which end effector 114 is in a closed position (FIG. 1C). As movable handle 122 moves toward the proximal position, arm 122a of movable handle 122 drives an inner shaft 116d of elongated shaft assembly 116, compression spring 116a, and collar 116c proximally, as indicated by arrow "C" to close jaw members 130, 132 of end effector 114. Inner shaft 116d extends distally from instrument housing 112 and couples to end effector 114 to selectively move jaw members 130, 132 between open and closed positions. Simultaneously, movable handle 122 tightens eccentric cam cable 210, drawing second end portion 210b of cable 210 proximally, as indicated by arrow "E," while urging first end portion 210a of cable 210 distally, as indicated by arrow "F," so that cable 210 causes eccentric cam 206 to pivot downwardly and forwardly relative to instrument housing 112 toward movable handle 122, as indicated by arrow "D." Also simultaneously, cable 208 cams and wraps around annular cam 204, namely, annular track 204a, as indicated by arrows "G," so that cable 208 facilitates movement of collar 116c in the proximal direction relative to instrument housing 112, as indicated by arrows "C."

In this regard, cam assembly 200 functions to change a jaw force ratio as movable handle 122 moves between a distal position and a proximal position (and/or as end effector 114/jaw members 130, 132 move(s) from an open position to a closed position). The jaw force ratio is a ratio of an amount of force imparted to jaw members 130, 132 over a predetermined increment of travel distance. Travel distance can be, for instance, an arc length of pivoting movement of moveable handle 122 as moveable handle 122 moves relative to instrument housing 112. Alternatively and/or additionally, travel distance can be measured based on movement of jaw members 130, 132 relative to one another. In one example, for each degree of pivoting movement of moveable handle 122 relative to instrument housing 112 through a first arc length, the amount of force imparted to jaw members 130, 132 can be X, whereas for each degree of pivoting movement of moveable handle 122 through second arc length adjacent to the first arc length, the amount of force imparted to jaw members 130, 132 can be 3×. More specifically, during initial movement of movable handle 122 toward a proximal position so that jaw members 130, 132 approximate from an open position to a closed position, cam assembly 200 can provide a jaw force ratio of 1:1, as dictated by the similar diameters of annular cable track 20a of annular cam 204 and annular portion 206b of eccentric cable track 206a. Further, when movable handle 122 moves through a predetermined arc length after jaw members 130, 132 are closed, cam assembly 200, namely eccentric cam 206 and cable 210 arrangement of cam assembly 200, may impart a jaw force ratio of 3:1, for instance. In this regard, with the jaw force ratio of 3:1, a user requires less hand force to compress jaw members 130, 132 together (see e.g., FIGS. 1C and FIG. 3B) such as when sealing tissue disposed between jaw members 130, 132 with electrosurgical energy transmitted to jaw members 130, 132.

After the user releases movable handle 122, for example, when finished sealing tissue and/or cutting tissue between jaw members 130, 132, compression spring 116a urges movable handle 122 toward the initial distal position (FIG. 3A) where cam assembly 200 is in an unactuated position. In the unactuated position of cam assembly 200, apex 206d of eccentric cam 206 is pointed in a proximal direction (FIG. 3A). By comparison, when movable handle 122 is in the proximal position (FIG. 3B) and cam assembly 200 is in an actuated position (e.g., fully or substantially fully actuated), apex 206d of eccentric cam 206 points in a downward direction (FIG. 3B).

In embodiments, the profile of eccentric cam 206 can have any suitable shape and/or configuration with varying diameters along an outer surface thereof to provide a changing jaw force ratio, for example, when eccentric cam 206 rotates at the same rate as annular cam 204. More particularly, the profile of eccentric cam 206 can be changed to achieve different movement and/or force ratios. Although annular cam 204 may be circular, in some embodiments, annular cam 204 may have any suitable shape and/or configuration, which may be the same and/or different from eccentric cam 206 in order to facilitate reduction in force required on the movable handle 122.

In certain embodiments, annular cam cable 208 and eccentric cam cable 210 may be portions of a single unitary cable and/or sub-portions of a plurality of different cables. As can be appreciated, any of the disclosed cables can be one or more wires, fibers, threads, filaments, chains, belts, linkages, etc., or combinations thereof, and which may be braided, sheathed, coated, etc., and/or otherwise joined together using any suitable joining technique.

In some embodiments, cam assembly 200 may include any number and/or configuration of linkages to achieve a similar "eccentric" relationship as detailed above.

In certain embodiments, cables 208, 210 and/or cams 204, 206 can be provided in any suitable arrangement, for example, so that annular cam 204 is connected to moveable handle 122 (e.g., indirectly and/or directly) and eccentric cam 206 is connected to collar 116c (e.g., indirectly and/or directly), or vice versa.

In some embodiments, compression spring 116a is contained at least partially, or entirely, within collar 116c.

In some embodiments, cam assembly 200 can include one or more pulleys in addition to, or in place of, one or more of cams 204, 206 and/or cables 208, 210.

As can be appreciated, securement of any of the components of the presently disclosed apparatus can be effectuated using known securement techniques such welding, crimping, gluing, fastening, etc.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical work stations and/or components thereof, reference may be made to U.S. Pat. No. 8,828,023, and PCT Application Publication No. WO2016/025132, the entire contents of each of which are incorporated by reference herein.

Persons skilled in the art will understand that the structures and methods specifically described herein and illustrated in the accompanying figures are non-limiting exemplary embodiments, and that the description, disclosure, and figures should be construed merely as exemplary of particular embodiments. It is to be understood, therefore, that this disclosure is not limited to the precise embodiments described, and that various other changes and modifications may be effected by one skilled in the art without departing from the scope or spirit of this disclosure. Additionally, it is envisioned that the elements and features illustrated or described in connection with one exemplary embodiment may be combined with the elements and features of another without departing from the scope of this disclosure, and that such modifications and variations are also intended to be included within the scope of this disclosure. Indeed, any combination of any of the disclosed elements and features is within the scope of this disclosure. Accordingly, the subject matter of this disclosure is not to be limited by what has been particularly shown and described.

The invention claimed is:

1. A forceps, comprising:
a housing including an actuator movably coupled to the housing;
an elongated shaft assembly coupled to the housing and extending distally to support a pair of jaw members at a distal end thereof, at least one of the jaw members selectively moveable relative to the other jaw member between a spaced apart position for manipulating tissue and a closed position for compressing tissue therebetween; and
a cam assembly supported in the housing and including an eccentric cam cable and an eccentric cam having an eccentric profile, the eccentric cam cable wrapped around the eccentric profile of the eccentric cam, operably coupled to the actuator, and positioned to rotate the eccentric cam upon movement of the eccentric cam cable, wherein rotation of the eccentric cam reduces an amount of force on the actuator required to move the jaw members to the closed position to compress tissue disposed between the jaw members, wherein the cam assembly further includes an annular cam positioned adjacent to the eccentric cam.

2. The forceps of claim 1, wherein the eccentric cam and the annular cam are disposed on a shaft that is pivotally supported within the housing.

3. The forceps of claim 2, wherein the eccentric cam includes an inner eccentric cam plate and an outer eccentric cam plate that are configured to maintain the eccentric cam cable on an eccentric track defined between the inner and outer eccentric cam plates.

4. The forceps of claim 3, wherein the eccentric track includes an annular portion and a triangular portion.

5. The forceps of claim 4, wherein the annular cam includes an annular track defined therein including substantially the same diameter as the annular portion of the eccentric track.

6. The forceps of claim 4, wherein the annular portion and the triangular portion of the eccentric track define a teardropped shaped profile.

7. The forceps of claim 5, further comprising an annular cam cable that is supported on the annular track of the annular cam.

8. The forceps of claim 7, wherein the elongated shaft assembly extends into the housing and supports an inner shaft that operatively couples to the pair of jaw members, the inner shaft supporting a collar that couples to the annular cam cable.

9. The forceps of claim 8, further comprising a compression spring supported on the inner shaft and engaged with the collar and an arm of the actuator to spring bias the actuator.

10. The forceps of claim 1, wherein the eccentric cam cable is wrapped around both the eccentric cam and the annular cam.

11. A forceps, comprising:
a housing including an actuator coupled to the housing and movable relative to the housing between a first position and a second position;
an elongated shaft assembly coupled to the housing and extending distally to an end effector, the end effector having a pair of jaw members movable between an open position and a closed position in response to movement of the actuator between the first position and the second position;
an annular cam supported in the housing and coupled to the elongated shaft assembly;
an eccentric cam coupled adjacent to the annular cam and positioned to rotate with the annular cam as the actuator moves between the first position and the second position; and
an eccentric cam cable connected to the actuator and positioned to move with the actuator to rotate the eccentric cam.

12. The forceps of claim 11, wherein the elongated shaft assembly includes an inner shaft, and wherein rotation of the annular cam causes the inner shaft to axially translate between distal and proximal positions relative to the housing to actuate the pair of jaw members.

13. The forceps of claim 12, further comprising an annular cam cable coupled to the annular cam and a collar supported on the inner shaft.

14. The forceps of claim 13, wherein the inner shaft supports a compression spring engaged with the collar and the actuator.

15. The forceps of claim 14, further comprising an eccentric cam cable coupled to the eccentric cam and to the actuator.

16. The forceps of claim 11, wherein the annular cam and the eccentric cam have different profiles.

17. The forceps of claim 16, wherein rotation of the eccentric cam changes a jaw force ratio as the actuator moves relative to the eccentric cam.

18. The forceps of claim 11, wherein the pair of jaw members are configured to receive electrosurgical energy to selectively seal tissue disposed between the pair of jaw members.

19. The forceps of claim 11, further comprising a knife assembly that is actuatable to sever tissue disposed between the pair of jaw members.

20. An electrosurgical system, comprising:
a generator; and
a forceps coupled to the generator and including:
a housing;
an actuator coupled to the housing;
an elongated shaft assembly extending distally from the housing to a pair of jaw members at a distal end thereof, the pair of jaw members disposed in electrical communication with the generator, the pair of jaw members movable between a spaced apart position for manipulating tissue and a closed position for compressing tissue therebetween; and
an eccentric cam coupled to the actuator and to an eccentric cam cable, the eccentric cam cable movable with the actuator and positioned to rotate the eccentric cam as the actuator moves between first and second positions relative to the housing, wherein rotation of the eccentric cam relative to the actuator reduces an amount of force on the actuator required to move the pair of jaw members to a closed position to compress tissue disposed between the pair of jaw members.

\* \* \* \* \*